US009655168B2

(12) United States Patent
Belongia et al.

(10) Patent No.: US 9,655,168 B2
(45) Date of Patent: May 16, 2017

(54) ELECTRICAL BARRIER FOR WAX WARMER

(71) Applicant: S.C. Johnson & Son, Inc., Racine, WI (US)

(72) Inventors: David C. Belongia, Burlington, WI (US); Dennis J. Beaumont, Libertyville, IL (US); Michael J. Goodrich, Oak Park, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 84 days.

(21) Appl. No.: 14/255,826

(22) Filed: Apr. 17, 2014

(65) Prior Publication Data

US 2015/0305089 A1    Oct. 22, 2015

(51) Int. Cl.
| | | |
|---|---|---|
| *A61L 9/03* | (2006.01) | |
| *H05B 1/02* | (2006.01) | |
| *H05B 3/26* | (2006.01) | |
| *H05B 3/00* | (2006.01) | |

(52) U.S. Cl.
CPC ............. *H05B 1/0252* (2013.01); *A61L 9/03* (2013.01); *H05B 3/0052* (2013.01); *H05B 3/26* (2013.01); *H05B 2203/02* (2013.01); *H05B 2203/022* (2013.01)

(58) Field of Classification Search
CPC .. A61L 9/03; A61L 9/035; A61L 9/037; F24F 11/00
USPC ........ 392/390–398, 386, 219, 429–441, 385; 239/34–60
See application file for complete search history.

(56) References Cited

U.S. PATENT DOCUMENTS

| | | | |
|---|---|---|---|
| 2,685,020 A | 7/1954 | Laibow | |
| 4,731,522 A | 3/1988 | Manchester | |
| 5,647,052 A | 7/1997 | Patel et al. | |
| 5,922,231 A | 7/1999 | Karst et al. | |
| 6,413,476 B1 * | 7/2002 | Barnhart | A61L 9/03 422/123 |
| 6,663,838 B1 * | 12/2003 | Soller | A01M 1/2088 422/120 |
| D485,341 S | 1/2004 | Wu | |
| D492,020 S | 6/2004 | Sevy et al. | |
| 6,756,567 B1 | 6/2004 | Suen | |
| 7,046,919 B2 | 5/2006 | Shimizu et al. | |
| 7,059,795 B2 | 6/2006 | Guillaume et al. | |
| 7,132,084 B1 | 11/2006 | Roumpos | |
| 7,133,605 B2 | 11/2006 | Niemeyer | |
| 7,252,805 B2 | 8/2007 | Hart et al. | |
| 7,329,839 B2 | 2/2008 | Palmer | |
| D579,645 S | 11/2008 | Guers-Neyraud | |
| D585,537 S | 1/2009 | Weggelaar | |
| D589,801 S | 4/2009 | Lablaine | |
| D603,034 S | 10/2009 | Thompson | |
| D604,627 S | 11/2009 | LaBlaine | |
| D665,066 S | 8/2012 | Browder | |
| 8,364,028 B1 | 1/2013 | Pesu et al. | |

(Continued)

OTHER PUBLICATIONS

PCT/US2015/026353 International Search Report and Written Opinion dated Oct. 14, 2015.

*Primary Examiner* — Michael Laflame, Jr.

(57) ABSTRACT

A wax warmer includes a body, an electrical assembly positioned within an interior space of the body, and a sleeve positioned within the interior space. The sleeve surrounds and provides a barrier to the electrical assembly.

9 Claims, 8 Drawing Sheets

(56) References Cited

U.S. PATENT DOCUMENTS

| | | | |
|---|---|---|---|
| D675,528 S | 2/2013 | Beaver | |
| 8,716,632 B1* | 5/2014 | Pesu | H05B 1/0269 |
| | | | 219/433 |
| 8,873,941 B2* | 10/2014 | Row | A61M 16/1075 |
| | | | 219/544 |
| 2001/0041317 A1* | 11/2001 | Frandsen | F21V 35/00 |
| | | | 431/289 |
| 2005/0016985 A1 | 1/2005 | Haas et al. | |
| 2005/0074358 A1* | 4/2005 | Hart | A01M 1/2083 |
| | | | 422/5 |
| 2005/0106077 A1* | 5/2005 | Hurwitz | A47G 27/02 |
| | | | 422/124 |
| 2005/0155985 A1* | 7/2005 | Meyer | A01M 1/2077 |
| | | | 222/146.2 |
| 2006/0163241 A1 | 7/2006 | Xiao | |
| 2006/0175425 A1* | 8/2006 | McGee | A01M 1/2033 |
| | | | 239/44 |
| 2006/0193611 A1* | 8/2006 | Ruiz Ballesteros | A61L 9/037 |
| | | | 392/394 |
| 2006/0219694 A1* | 10/2006 | Wu | A61L 9/03 |
| | | | 219/400 |
| 2007/0031298 A1 | 2/2007 | Roumpos et al. | |
| 2009/0004614 A1* | 1/2009 | Furner | A61L 9/03 |
| | | | 431/291 |
| 2010/0096376 A1 | 4/2010 | Hsiao | |
| 2010/0270943 A1* | 10/2010 | Cook | A61L 9/03 |
| | | | 315/291 |
| 2011/0110072 A1* | 5/2011 | Hsiao | A61L 9/03 |
| | | | 362/96 |
| 2011/0110118 A1* | 5/2011 | Hsiao | A61L 9/03 |
| | | | 362/643 |
| 2012/0024837 A1 | 2/2012 | Thompson | |
| 2012/0183280 A1 | 7/2012 | Kowalec et al. | |
| 2012/0318779 A1 | 12/2012 | Juarez | |
| 2012/0318780 A1* | 12/2012 | Juarez | H05B 3/26 |
| | | | 219/209 |
| 2013/0020307 A1 | 1/2013 | Ashton et al. | |
| 2013/0170184 A1 | 7/2013 | Browder et al. | |
| 2013/0266297 A1* | 10/2013 | Ihle | A01M 1/2077 |
| | | | 392/386 |
| 2014/0118993 A1* | 5/2014 | Chen | G02B 6/0001 |
| | | | 362/96 |
| 2014/0133132 A1* | 5/2014 | Hsiao | A61L 9/03 |
| | | | 362/96 |
| 2014/0158790 A1* | 6/2014 | Gordon | A01M 1/2044 |
| | | | 239/44 |
| 2015/0010293 A1* | 1/2015 | Newman | A61L 9/032 |
| | | | 392/393 |
| 2015/0108243 A1* | 4/2015 | Bourne | A61L 9/125 |
| | | | 239/58 |

\* cited by examiner

ELECTRICAL BARRIER FOR WAX WARMER

CROSS REFERENCE TO RELATED APPLICATIONS

Not applicable

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present disclosure generally relates to an electrical barrier for a wax warmer, and more specifically, to an electrical barrier that inhibits a user from contacting live electrical components when a body of the wax warmer is broken or damaged.

2. Description of the Background of the Invention

Candles have been used for centuries to provide illumination and pleasant aromas to the surrounding environment. At its most basic level, a candle consists of a wick dipped in wax. The wick is lit and provides light while the burning or melting wax may provide a pleasant aroma. Alternatively, unscented or scented candles or wax melts can be placed in a warmer. These candles or warmers may also be used to provide more than just illumination and/or pleasant fragrances. For instance, candles and warmers may be placed outside around a patio or deck. The wax or oil may include materials with insect repellant properties along with providing a pleasant aroma and/or illumination. Generally, users can burn or warm waxes and oils to provide desired effects to the surrounding atmosphere or environment.

Traditional warmers and candles that utilize a live flame may have some drawbacks. Candles may be forgotten and left unsupervised and may represent a fire hazard. Also, a candle flame may be extinguished with a slight breeze or gust of wind. An additional drawback associated with candles is the inability to control the intensity of the heat being provided to the scented material. A candle flame is not easily adjustable and thus the amount of heat the flame provides to the infused wax or oil does not allow a user to vary the strength of the fragrance introduced into the surrounding environment.

Some attempts have been made to overcome the aforementioned drawbacks associated with live flame warmers and candles through the use of electric wax warmers. An electric wax warmer consists of a heater in thermal contact with a reservoir for holding a wax melt or infused oil. The heater replaces the candle in a traditional warmer and melts the wax or heats the oil in the reservoir, resulting in the same benefits as previously mentioned. The lack of a flame reduces the risks associated with traditional warmers and candles. Another advantage may be the temperature of the heater in an electric wax warmer can be adjusted. This provides the user with more control over the amount of fragrant or other materials introduced into the surrounding environment. Electric wax warmers also have more consistent performance indoors and outdoors and are less messy than traditional candles and warmers.

Electric wax warmers may have significant advantages over traditional warmers and candles, however, they may also have some drawbacks. Many of the traditional electric wax warmers include a housing, commonly constructed of a ceramic material, that encloses the various electrical components necessary for heating the wax melt or infused oil. Thus, if the ceramic housing is broken, the various electrical components may be exposed allowing a user to come into contact with live electrical components.

Attempts have been made by some standards setting organizations to require such ceramic housings to pass a ball impact test. For example, the UL 283 standard for air fresheners and deodorizers requires ceramic wax warmers to undergo an impact performance test using a 535 gram, 5.08 centimeter diameter smooth, solid steel ball that is dropped from a specified height of 60 centimeters. Once the steel ball is dropped onto the ceramic housing, a finger probe may be used, assuming the ceramic housing is damaged, in an attempt to contact the electrical components of the wax warmer. According to the UL 283 standard, if the finger probe can contact the electrical components through the broken ceramic housing, the wax warmer does not pass the ball impact test.

Interestingly, traditional wax warmers often do not pass the ball impact test required by the UL 283 standard, leaving the users of wax warmers at risk. Further, other wax warmers must use stronger or alternative materials to resist cracking, which increases the cost of manufacturing. Therefore, there is a need for an electric wax warmer that overcomes the aforementioned drawbacks.

The present disclosure overcomes some of the aforementioned drawbacks by providing an electrical barrier for a wax warmer that is in compliance with the UL 283 standard. Thus, the present disclosure satisfies the existing need for a wax warmer that includes an electrical barrier to inhibit a user from contacting live electrical components. Further still, the present disclosure satisfies the need for an electrical barrier for a wax warmer that is easy to manufacture, thus keeping manufacturing costs and material usage down.

SUMMARY OF THE INVENTION

According to one aspect, a wax warmer includes a body, an electrical assembly positioned within an interior space of the body, and a sleeve. The sleeve is positioned within the interior space and surrounds the electrical assembly to provide a barrier to the electrical assembly.

According to another aspect, an electrical barrier for a wax warmer includes an annular sleeve for positioning within a body of a wax warmer to surround an electrical assembly. The annular sleeve comprises 100% of a polymeric material having a thermal rating of at least 230 degrees Fahrenheit and a modulus of elasticity of between 1.5 GPa and 2.6 GPa. The annular sleeve also has a diameter of at least 5.7 centimeters.

According to a further aspect, a wax warmer includes a body, an electrical assembly positioned within an interior space of the body, and an annular sleeve positioned within the interior space and surrounding the electrical assembly.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
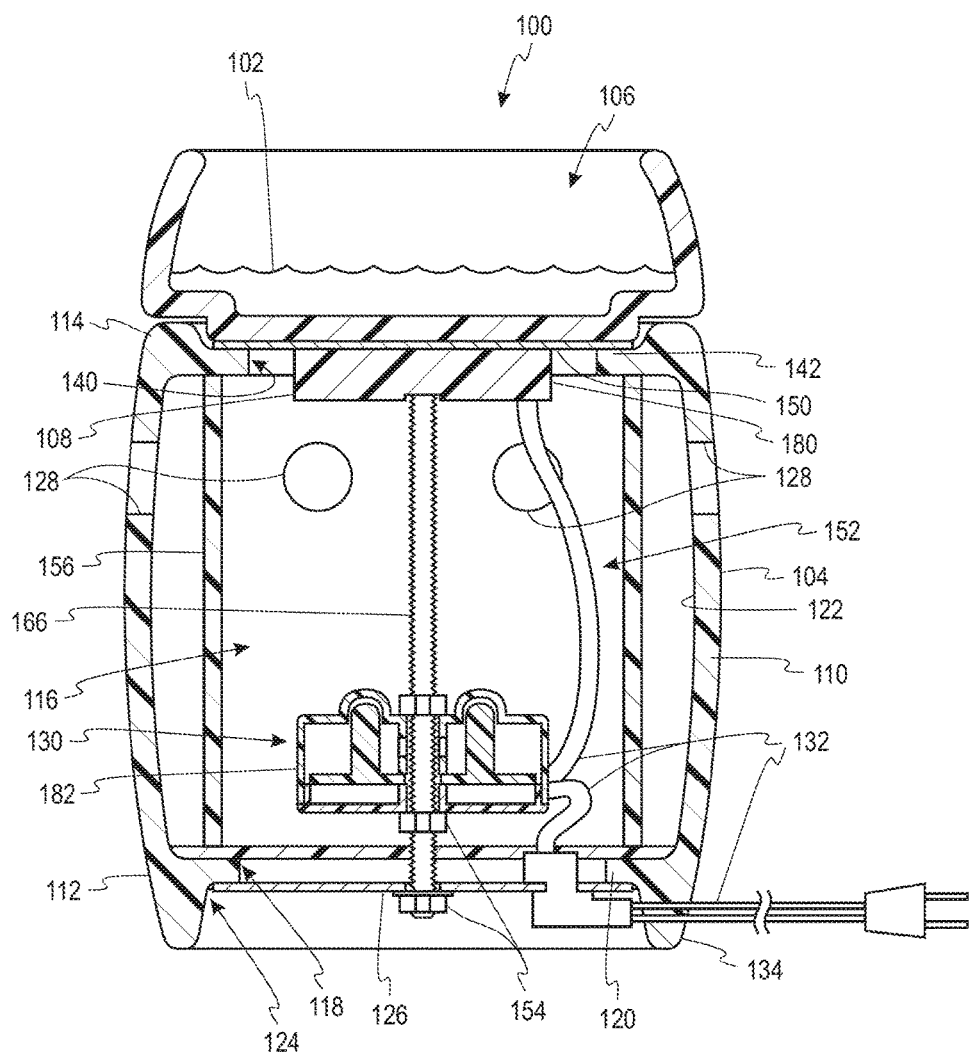
FIG. 1 is a cross-sectional side elevational view of a wax warmer.

Referring to FIG. 1, a wax warmer 100 is depicted. The wax warmer 100 is designed to heat a wax melt 102 and thereby release a fragrance or other material contained therein into the surrounding environment. The wax warmer 100 generally includes a body 104, a reservoir 106, and a heater assembly 108. The body 104 is fashioned to house the heater assembly 108 and provide a support structure for the reservoir 106. The wax warmer 100 is generally described to include the aforementioned components, but the wax warmer 100 may be adapted to add or remove various components according to specific user requirements.

Still referring to FIG. 1, the body 104 includes a sidewall 110 having a bottom end 112 and a top end 114. In the present embodiment, the sidewall 110 is generally cylindrical in shape and defines an interior space 116. The bottom end 112 defines a first opening 118. A lip 120 extends from an inner surface 122 of the sidewall 110. The bottom end 112 and the lip 120 form a recess 124 adapted to receive a base plate 126 that is disposed adjacent the bottom end 112 of the body 104. Portions of the bottom end 112 of the body 104 may include extensions (not shown) or other structures (feet, pads, structures with high coefficients of friction, etc.) generally known to those having ordinary skill in the art to provide stability to the wax warmer 100.

The sidewall 110 further includes one or more apertures 128 provided therein. The apertures 128 may be adapted to receive a light emissive or transmissive cover (not shown) and/or an indicator, such as an LED, or sensor (not shown). For example, the apertures 128 may allow light, provided by an electrical light source 130, from the interior space 116 to be visible through the apertures 128. Additionally, one or more of the apertures 128 may be fully or partially unobstructed to facilitate cooling of the body 104 and/or the flow of air through the interior space 116 of the wax warmer 100. The apertures 128 may be any desired shape and size for aesthetics, cooling, and light passage. For example, and without limitation, the apertures 128 may be circular (as shown in FIG. 1), triangular, rectangular, polygonal, star-shaped, crescent-shaped, irregularly-shaped, flower-shaped, etc. A second aperture 134 is also provided proximal to the bottom end 112 of the sidewall 110. Preferably, the second aperture 134 provides a pass-through for an electrical cord 132 in electrical communication with the electrical light source 130 and the heater assembly 108.

Referring still to FIG. 1, a second opening 140 is provided at the top end 114 of the sidewall 110. The second opening 140 is bounded by a shoulder 142 extending radially inwardly from the inner surface 122 of the sidewall 110. The second opening 140 and the shoulder 142 are adapted to receive the heater assembly 108 and the reservoir 106.

It has been contemplated that the body 104 and the reservoir 106 are preferably made from a ceramic material. However, any other materials as known to those having ordinary skill in the art may be used, such as plastic, metal, stone or other natural materials, etc. The body 104 and the reservoir 106 may take any geometric shape, e.g. a square, to provide different appearances. Further, the exterior surfaces of the body 104 and the reservoir 106 may be provided with any type of surface indicia, raised patterns, or any other decorations to configure the wax warmer 100 for aesthetic purposes.

With continued reference to FIG. 1, an electrical assembly 152 of the wax warmer 100 described above may be at least partially disposed within the interior space 116 of the body 104. The electrical assembly 152 may include the heater assembly 108 and the electrical light source 130. In some embodiments, structural components may hold some of the various components in place. For example, a threaded rod 166 may extend through the base plate 126 and the electrical light source 130 and may abut against the heater assembly 108. At least one nut 154 may hold the threaded rod 166 and the various components in place.

The heater assembly 108 may be positioned within the body 104 proximate the second opening 140 such that the heater assembly 108 may heat the wax melt 102 in the reservoir 106. In some embodiments, the electrical light source 130 may be positioned within the body 104 at a location distant to that of the heater assembly 108, such as proximate the first opening 118 of the bottom end 112. In other embodiments, the electrical light source 130 may be positioned within the body 104 at a location proximate the heater assembly 108. The heater assembly 108 may be a heat source such as a resistance heater, an incandescent light bulb, a PTC heater, or any other heater known to one in the art.

In one preferred embodiment, the wax warmer 100 includes a top plate 150 under the reservoir 106. The top plate 150 may be formed from a metallic material and disposed adjacent the top end 114 of the body 104. The heater assembly 108 may be abutted against or otherwise thermally coupled to a surface of the top plate 150. By way of non-limiting examples, the heater assembly 108 may be coupled to the top plate 150 with an adhesive, with a mechanical connection (e.g., a clip, screw, interference fit, etc.), by being pushed against the top plate 150 with the threaded rod 166 (as shown), or any combination thereof. In embodiments in which the reservoir 106 and the body 104 are separate and detachable, the top plate 150 may be attached to one of the reservoir 106 or the body 104 or neither. In some embodiments, the wax warmer 100 may not include the top plate 150. In such embodiments, the heater assembly 108 may abut directly against a bottom of the reservoir 106.

Figure 2:
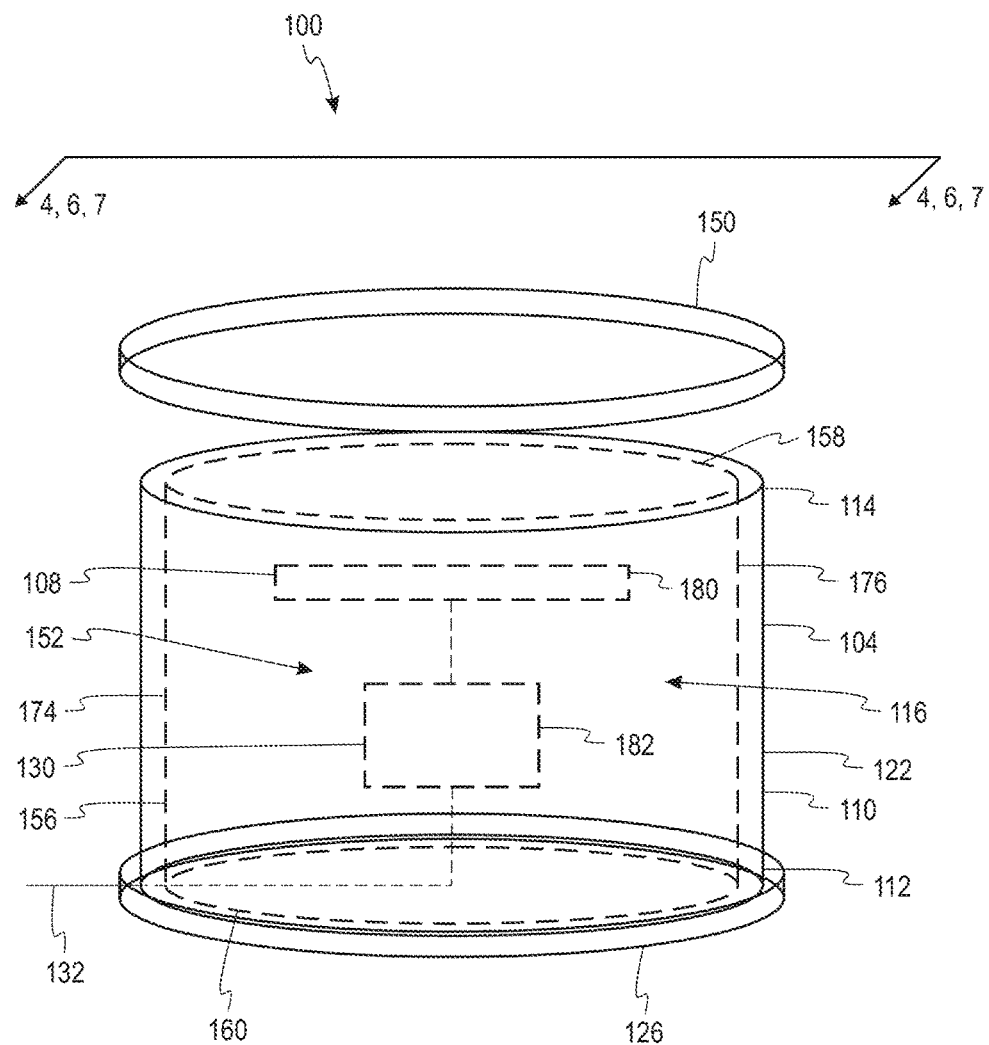
FIG. 2 is a schematic view of a wax warmer with an electrical barrier.

Turning now to FIG. 2, a simplified schematic diagram of the wax warmer 100 is shown. The wax warmer 100 includes substantially the same components as described with reference to FIG. 1, therefore similar reference numerals will be used.

Figure 9:
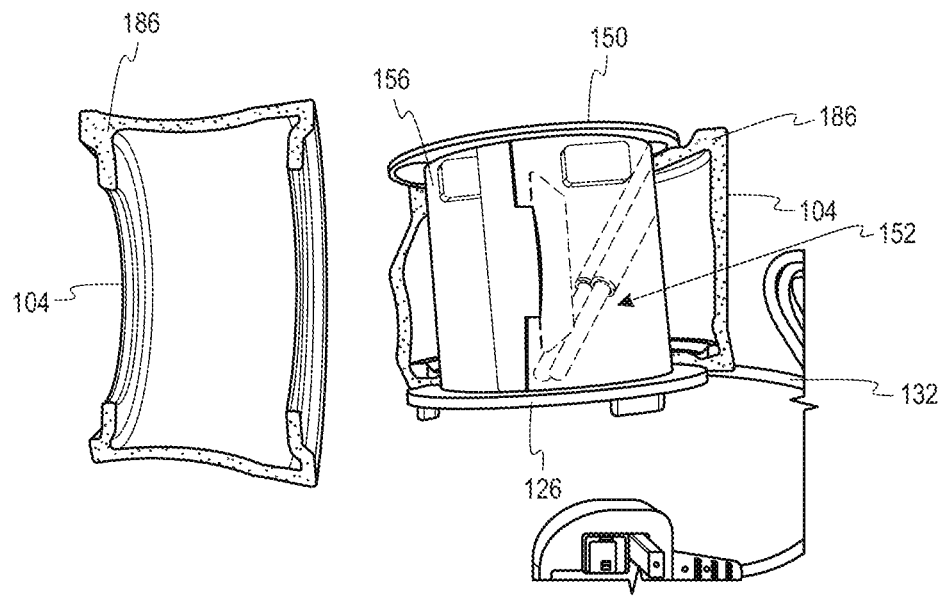
FIG. 9 is an image of the wax warmer of FIG. 8 after the ball impact test showing an electrical barrier.

An electrical barrier 156 is positioned inside the body 104 of the wax warmer 100 in the embodiment shown in FIG. 2 (see also FIG. 1). The electrical barrier 156 may take the form of an annular sleeve, for example, and surround the electrical assembly 152. Thus, if the body 104 of the wax warmer 100 is damaged or broken, as shown in FIG. 9, the electrical assembly 152, including the heater assembly 108 and electrical light source 130, are not exposed to a user of the wax warmer 100. In addition, the electrical barrier 156 ensures that the wax warmer 100 is in compliance with standards related to air fresheners and deodorizers, such as the UL 283 standard, as will be described in further detail below.

Figure 3A:
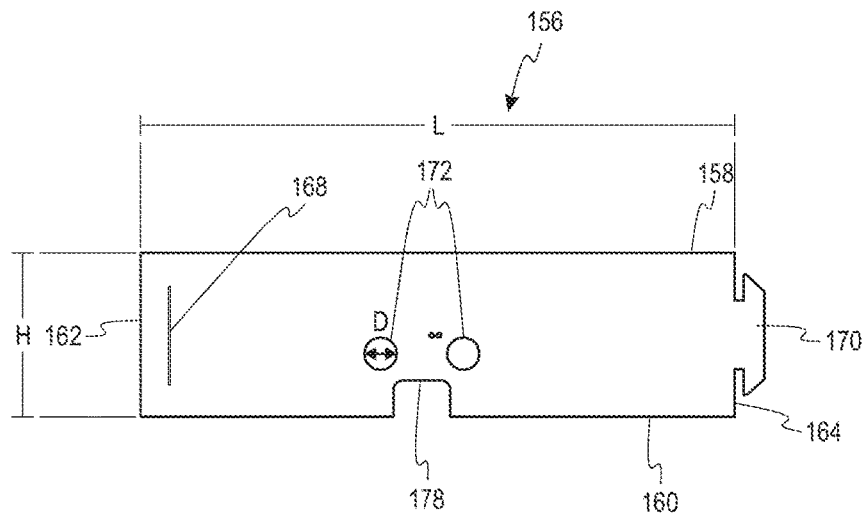
FIG. 3A is a side elevational view of an electrical barrier layout according to one embodiment of the disclosure.
Figure 3B:
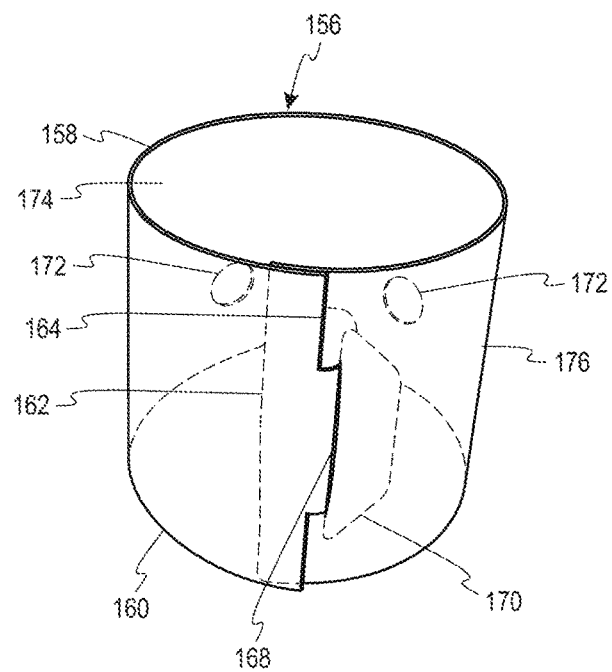
FIG. 3B is a perspective view of the electrical barrier of FIG. 3A coupled together to form a generally cylindrical shape.

A first embodiment of the electrical barrier 156 is shown in FIGS. 3A and 3B. The electrical barrier 156 can begin as a flat, substantially rectangular layout, as shown in FIG. 3A having a length dimension L and a height dimension H. The length dimension L and the height dimension H may vary depending on the dimensions of the particular wax warmer 100 the electrical barrier 156 is used in. In a preferred embodiment, the length dimension L is about 22.5 centimeters, and the height dimension H is about 5.7 centimeters. The electrical barrier 156 may have a thickness dimension T (see FIG. 4) that is preferably between about 0.025 centimeters and about 0.15 centimeters. However, the length dimension L may be any suitable length to allow the electrical barrier 156 to fit within the body 104 of the wax warmer 100. Similarly, the height dimension H may be of any height to allow the electrical barrier 156 to fit within the body 104 and not extend beyond the base plate 126 or the top plate 150 of the wax warmer 100. Likewise, the thickness dimension T may vary depending on the specific wax warmer 100 that the electrical barrier 156 is used in. For example, depending on the heater assembly 108 used in a particular wax warmer 100, the thickness dimension T may change in order to withstand a variety of heat outputs.

Turning again to FIG. 3A, the electrical barrier 156 includes a top edge 158 and a bottom edge 160 that extend the length dimension L. In the present embodiment, the top edge 158 is parallel to the bottom edge 160. A first side edge 162 and a second side edge 164 extend about the height dimension H. In the present embodiment, the first and second side edges 162, 164 are substantially parallel to one another. A groove 168 is provided adjacent to the first side edge 162, and a tongue portion 170 is provided adjacent to the second side edge 164. As shown in FIG. 3B, the groove 168 is configured to receive the tongue portion 170 to form a substantially cylindrical electrical barrier 156. Alternatively, the first side edge 162 and the second side edge 164 may be heat sealed, adhered, or coupled together using any suitable mechanical fastener (e.g., a staple or a rivet). In yet another alternative embodiment, the first side edge 162 and the second side edge 164 may be integrally molded together to form the electrical barrier 156.

Figure 4:
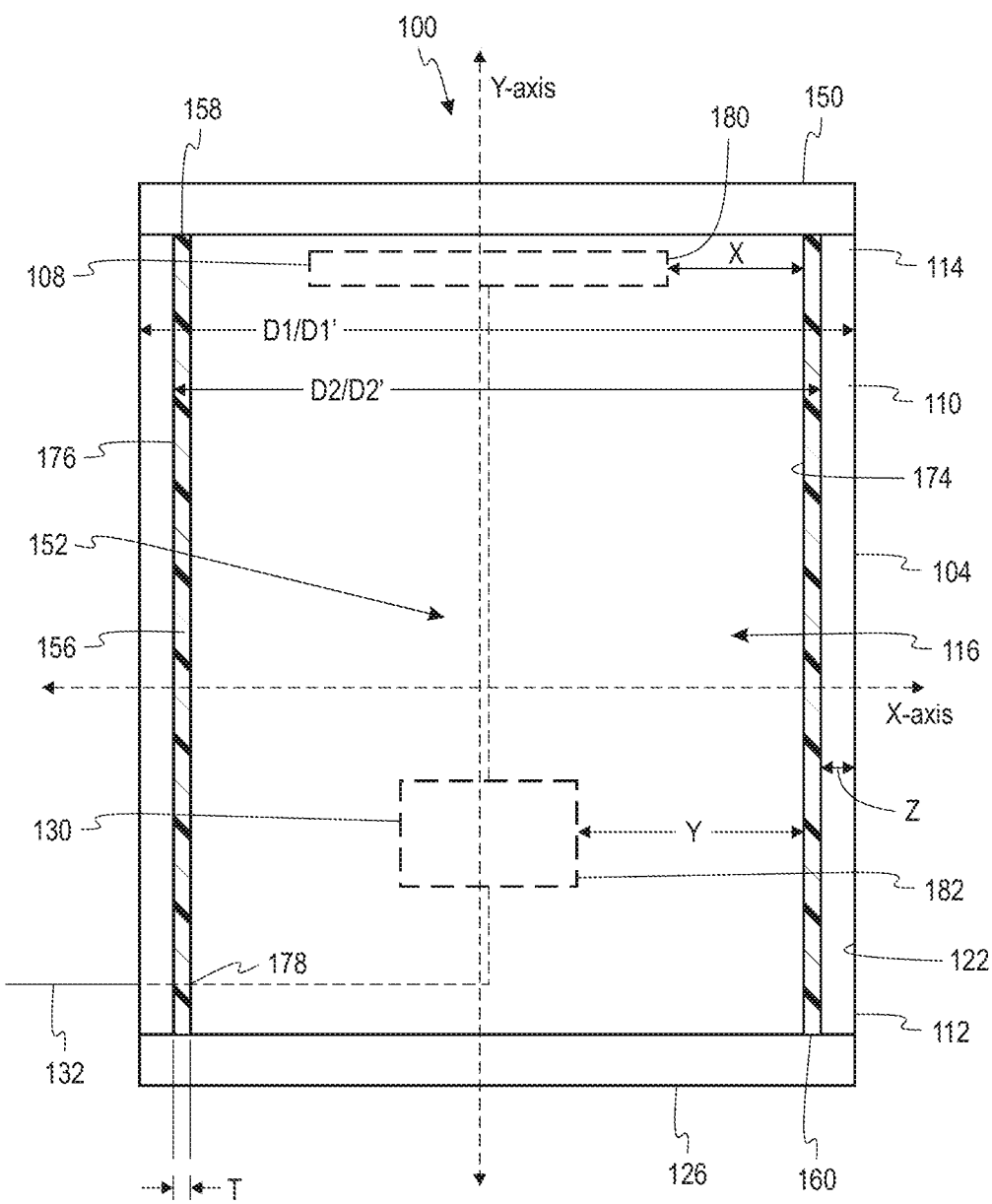
FIG. 4 is a cross-sectional view of the wax warmer taken generally along the line 4-4 of FIG. 2 with the electrical barrier in a first position.

In some embodiments, the electrical barrier 156 may take the form of a sleeve that has a substantially circular cross-section when taken through a horizontal axis (axis-x in FIG. 4). In other embodiments, the horizontal cross-section of the electrical barrier 156 is oval, circular, curvilinear, triangular, or any suitable shape in order to shield the electrical assembly 152. In the embodiment shown in FIGS. 3A and 3B the electrical barrier 156 is a right circular cylinder. However, the electrical barrier 156 can also take the form of an elliptic cylinder, an oblique cylinder, a parabolic cylinder, a hyperbolic cylinder, etc.

Still referring to FIGS. 3A and 3B, the electrical barrier 156 may include one or more apertures 172 that extend from an interior surface 174 to an exterior surface 176 of the electrical barrier 156. The one or more apertures 172 may include a diameter D that is not to exceed 0.95 centimeters. In other embodiments, the diameter D of the one or more apertures 172 is between about 0.64 centimeters and about 0.95 centimeters. A maximum diameter D is established such that in the event the body 104 of the wax warmer 100 is broken or damaged, a user is inhibited from contacting any of the components of the electrical assembly 152. Or, alternatively, during a standardized ball impact test, a finger probe (not shown) is inhibited from contacting any of the components of the electrical assembly 152 to maintain compliance with the UL 283 standard, for example.

The purpose of the one or more apertures 172 disposed on the surfaces 174, 176 of the electrical barrier 156 is to allow light, provided by the electrical light source 130, to be visible through the apertures 128 on the body 104. Additionally, the apertures 172 may facilitate cooling of the body 104 as heated air builds up within the interior space 116 during use of the wax warmer 100. The apertures 172 may be any desired shape for aesthetics, cooling, and light passage. The electrical barrier 156 may further include a slot 178, as shown in FIG. 3A, disposed along the bottom edge 160 of the electrical barrier 156. The slot 178 may be substantially sized so as to provide a passage for the electrical cord 132 to pass through the electrical barrier 156 and through the second aperture 134 (see FIG. 1) of the body 104.

Figure 5A:
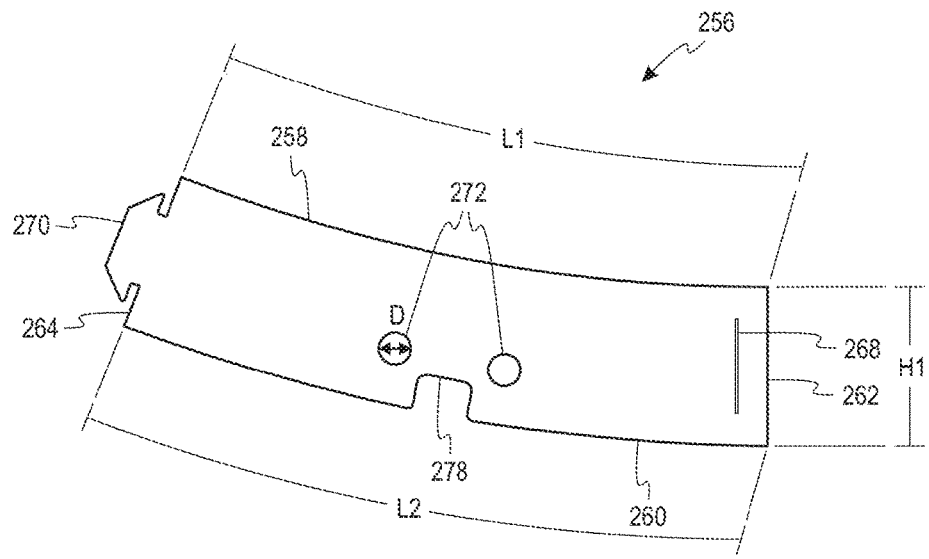
FIG. 5A is a side elevational view of an electrical barrier layout according to another embodiment of the disclosure.
Figure 5B:
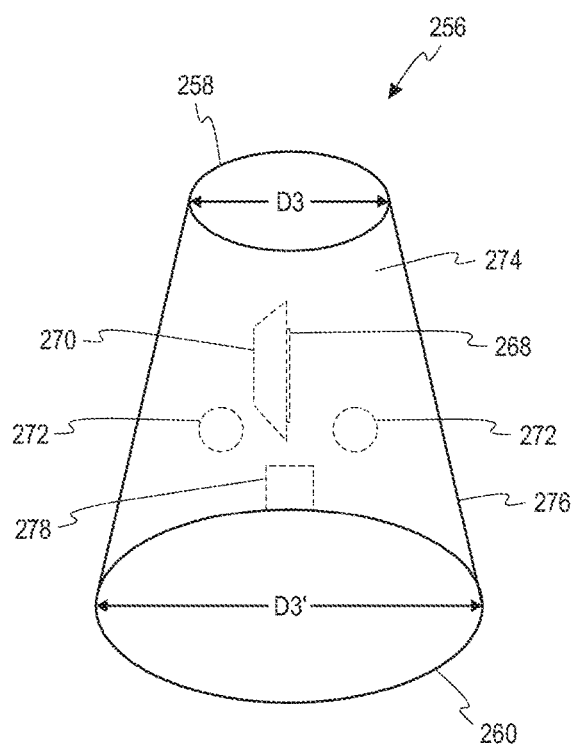
FIG. 5B is a perspective view of the electrical barrier of FIG. 5A coupled together to form a generally frusto-conical shape.

In an alternative embodiment, as shown in FIGS. 5A and 5B, a non-cylindrical electrical barrier 256 is provided that is substantially frusto-conical shaped. Similar to the cylindrical shaped electrical barrier 156, the frusto-conical shaped electrical barrier 256 can begin as a flat layout, as shown in FIG. 5A. Because the electrical barrier 256 is frusto-conical shaped, the top edge 258 may be slightly curved and have a length dimension L1, and the bottom edge 160 may also be slightly curved and have a length dimension L2. The length dimension L1 is measured as a curved line from the first side edge 262 to the second side edge 264 along the top edge 258. Similarly, the length dimension L2 is measured as a curved line from the first side edge 262 to the second side edge 264 along the bottom edge 260. Thus, the length dimension L1 is less than the length dimension L2. In a preferred embodiment, the length dimension L1 is about 20.9 centimeters, and the length dimension L2 is about 22.5 centimeters. The electrical barrier 256 also includes a height dimension H1 along the first side edge 262 and the second side edge 264 that is about 5.7 centimeters. The height dimension H1 is measured from the top edge 258 to the bottom edge 260 along either of the side edges 262, 264. The length dimensions L1 and L2 and the height dimension H1 may vary depending on the dimensions of the particular wax warmer 100 the electrical barrier 256 is used in. Thus, the length dimensions L1 and L2 may be any suitable length to allow the electrical barrier 256 to fit within the body 104 of the wax warmer 100. Similarly, the height dimension H1 may be of any height to allow the electrical barrier 256 to fit within the body 104 and not extend beyond the base plate 126 or the top plate 150. The electrical barrier 256 may have a thickness dimension (not shown) that is substantially the same as the thickness dimension T (see FIG. 4) of the cylindrical electrical barrier 156.

Due to the varying length dimensions L1 and L2, the frusto-conical shaped electrical barrier 256 has a minor diameter D3 at the top edge 258 that is less than a major diameter D3' at the bottom edge 260 (see FIG. 5B). In one embodiment, the minor diameter D3 is about 6.4 centimeters, and the major diameter D3' is about 6.7 centimeters. In contrast, the cylindrical shaped electrical barrier 156, as shown in FIG. 4, includes a uniform diameter D2 at the top end 114 and the bottom end 112 of the wax warmer 100 (see FIG. 4). The diameter D2 may be, in one embodiment, at least about 5.7 centimeters. However, the minor and major diameters D3 and D3', and the diameter D2, can vary depending on the aesthetic design, for example, of the wax warmer 100. Thus, the minor and major diameters D3 and D3' and the diameter D2 may be any suitable size to allow the frusto-conical shaped electrical barrier 256 or the cylindrical shaped electrical barrier 156 to fit within the body 104 of the wax warmer 100.

Referring again to FIGS. 5A and 5B, a groove 268 may be provided adjacent to the first side edge 262, and a tongue portion 270 may be provided adjacent to the second side edge 264. As shown in FIG. 5B, the groove 268 is configured to receive the tongue portion 270 to form the substantially frusto-conical shaped electrical barrier 256. Alternatively, the first side edge 262 and the second side edge 264 may be heat sealed, adhered, or coupled together using any suitable mechanical fastener (e.g., a staple or a rivet). In yet another alternative embodiment, the first side edge 262 and the second side edge 264 may be integrally molded together to form the electrical barrier 256.

Still referring to FIGS. 5A and 5B, the electrical barrier 256 may include one or more apertures 272 that extend from an interior surface 274 to an exterior surface 276 of the electrical barrier 256. The one or more apertures 272 may include a diameter D that is not to exceed 0.95 centimeters for the same reasons as previously described. In other embodiments, the diameter D of the one or more apertures 272 is between about 0.64 centimeters and about 0.95 centimeters.

The electrical barriers 156 and 256 of the present embodiments may be constructed of a polymeric material (e.g., polycarbonate, polypropylene, etc.), a mica material, or a horizontal burning (HB) material, for example. In some embodiments, the electrical barriers 156 and 256 may be constructed of any suitable flexible material. However, it is contemplated that a rigid material, such as a mica material, may be used for the electrical barriers 156 and 256.

The material of the electrical barriers 156 and 256 preferably includes a specific melting temperature above the maximum heat output of the heater assembly 108 used within the wax warmer 100. More preferably, the material of the electrical barriers 156 and 256 has a specific melting temperature above the combined heat output of the electrical assembly 152, which may include one or more of a heater(s), a light(s), a sensor(s), or other electrical component(s) capable of outputting heat. Therefore, the electrical barriers 156 and 256 preferably have a melting temperature between about 350 degrees Fahrenheit and about 510 degrees Fahrenheit. For example, in one non-limiting embodiment, the electrical light source 130 may provide a heat output ranging from about 10 watts to about 20 watts. Similarly, the heater assembly 108 may include a resistive heater, which has a heat output ranging from about 10 watts to about 20 watts.

Turning now to FIG. 4, the electrical barrier 156 is shown positioned within the body 104 of the wax warmer 100 and surrounding the electrical assembly 152. In some embodiments, the electrical barrier 156 is positioned a distance X from the electrical assembly. In the present scenario, the distance X may be defined as the distance from the interior surface 174 of the electrical barrier 156 to an exterior surface 180 of the heater assembly 108. The distance X may be measured in a horizontal plane defined by the x-axis shown in FIG. 4. Additionally, or alternatively, the electrical barrier 156 is positioned a distance Y from the electrical light source 130. The distance Y may be defined as the distance from the interior surface 174 of the electrical barrier 156 to an exterior surface 182 of the electrical light source 130. The distance Y may also be measured in a horizontal plane defined by the x-axis shown in FIG. 4. In one embodiment, the distance Y is 0.5 centimeters. In a preferred embodiment, the distance X is a minimum distance of about 0.3 centimeters. In some embodiments, however, minimum distances for X and Y may vary depending on the specific heater assembly 108 or electrical light source 130 used in the wax warmer 100.

The minimum distances X and Y may, in some embodiments, be directly correlated to a ratio of the heat output of the heater assembly 108 or the electrical light source 130 (as measured in watts) to the predetermined melting temperature (as measured in degrees Fahrenheit) of the material of the electrical barrier 156. In a preferred embodiment, the ratio of the heat output to the predetermined melting temperature is between about 0.02 and 0.05. Thus, the higher the heat output produced by either the heater assembly 108 or the electrical light source 130, the greater the distance X and/or Y will be.

In one specific embodiment, the electrical barriers 156 and 256 may be comprised of 100% polymeric materials, which may include one or more materials, and have a thermal rating of at least 230 degrees Fahrenheit and a modulus of elasticity of between 1.5 GPa and 2.6 GPa. Further, in this contemplated embodiment, the electrical barrier 156, 256 has a diameter, or minor diameter, of at least 5.7 centimeters Still referring to FIG. 4, the electrical barrier 156 may be positioned a distance Z from the sidewall 110 of the body 104. The distance Z may be measure from the exterior surface 176 of the electrical barrier 156 to the inner surface 122 of the sidewall 110. In an alternative embodiment, the electrical barrier 156 may be in direct contact with the inner surface 122 of the sidewall 110. However, regardless of the distance Z, the diameter D2 of the electrical barrier 156 is less than a diameter D1 of the body 104 to allow the electrical barrier 156 to be positioned within the body 104. Similarly, with reference to the frusto-conical shaped electrical barrier 256 (see FIGS. 5A and 5B), the diameters D3 and D3' are less than the diameter D1 of the body 104.

Figure 6:
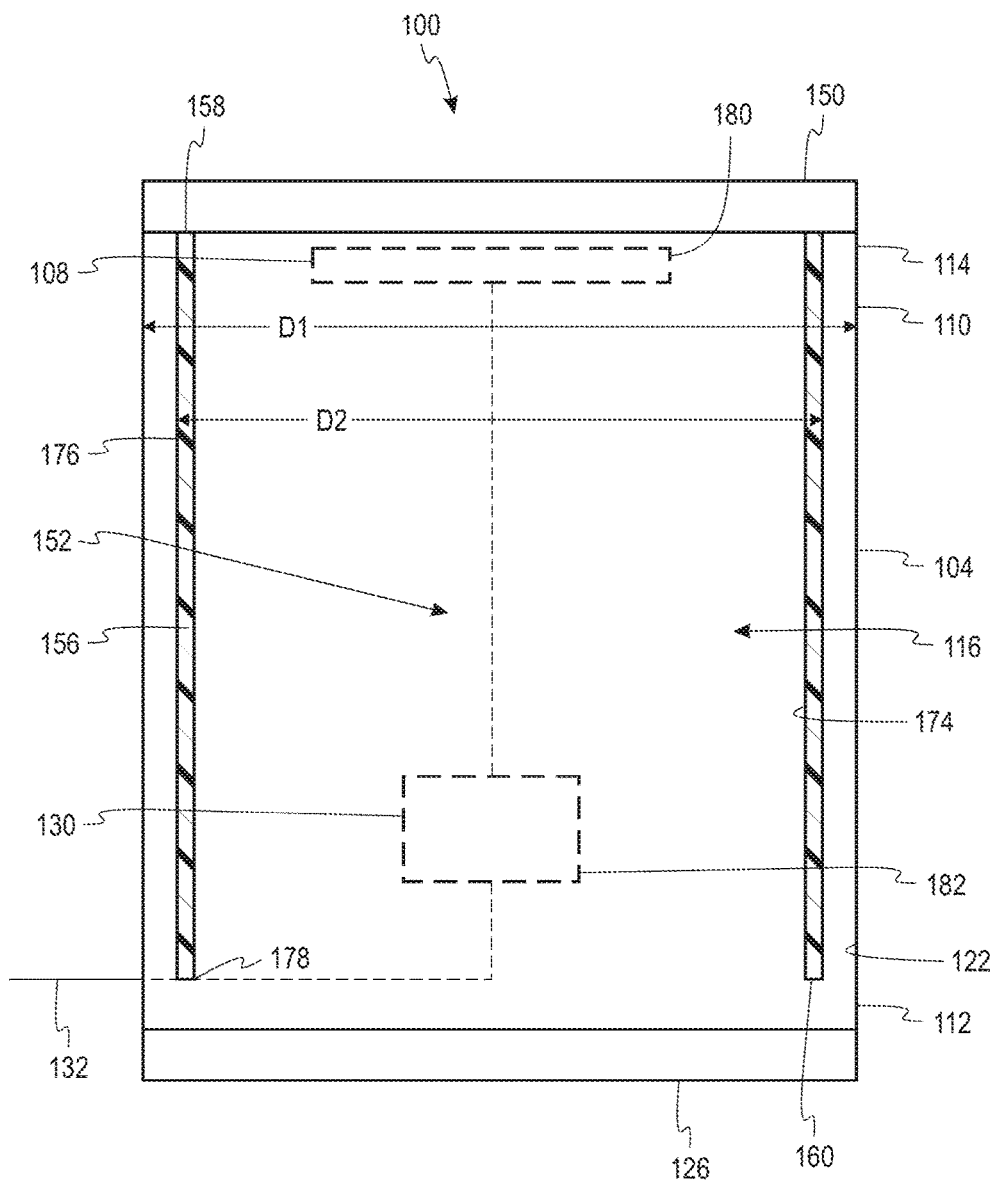
FIG. 6 is a cross-sectional view of the wax warmer taken generally along the line 6-6 of FIG. 2 with the electrical barrier in a second position.
Figure 7:
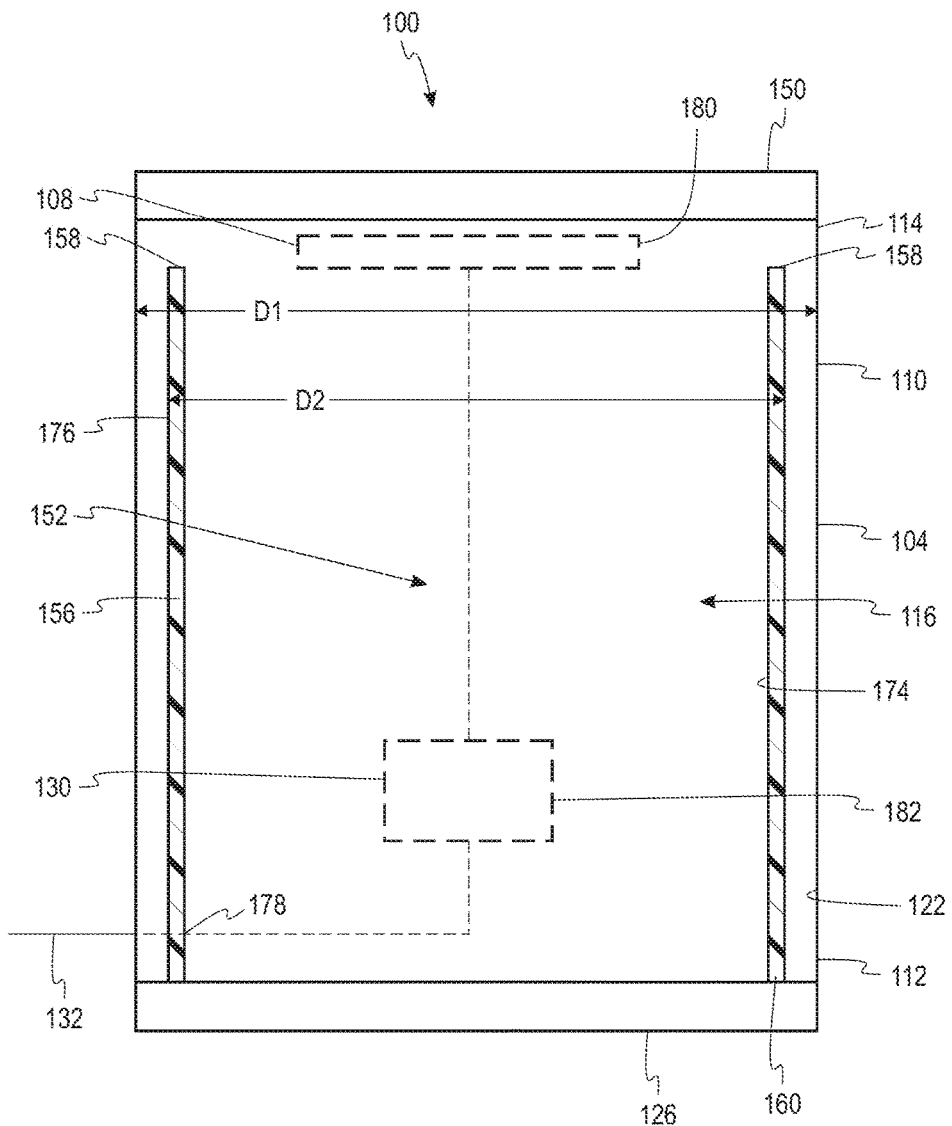
FIG. 7 is a cross-sectional view of the wax warmer taken generally along the line 7-7 of FIG. 2 with the electrical barrier in a third position.

As shown in FIG. 4, the top edge 158 of the electrical barrier 156 is in direct contact with the top plate 150, and the bottom edge 160 is in direct contact with the base plate 126. In an alternative embodiment, as shown in FIG. 6, the top edge 158 of the electrical barrier 156 is in direct contact with the top plate 150, and the bottom edge 160 is not in direct contact with the base plate 126, such that the electrical barrier 156 extends from the top plate 150 toward the bottom end 112 of the body 104. In yet another alternative embodiment, as shown in FIG. 7, the top edge 158 of the electrical barrier 156 is not in direct contact with the top plate 150, and the bottom edge 160 is in direct contact with the base plate 126, such that the electrical barrier 156 extends from the base plate 126 toward the top end 114 of the body 104. When either of the edges 158 and 160 are in direct contact with either of the plates 126 and 150, the connection can be made by a press fit, interference fit, integral molding or extrusion, or any other means providing for a substantially immovable fit as would be known to one of ordinary skill in the art.

Figure 8:
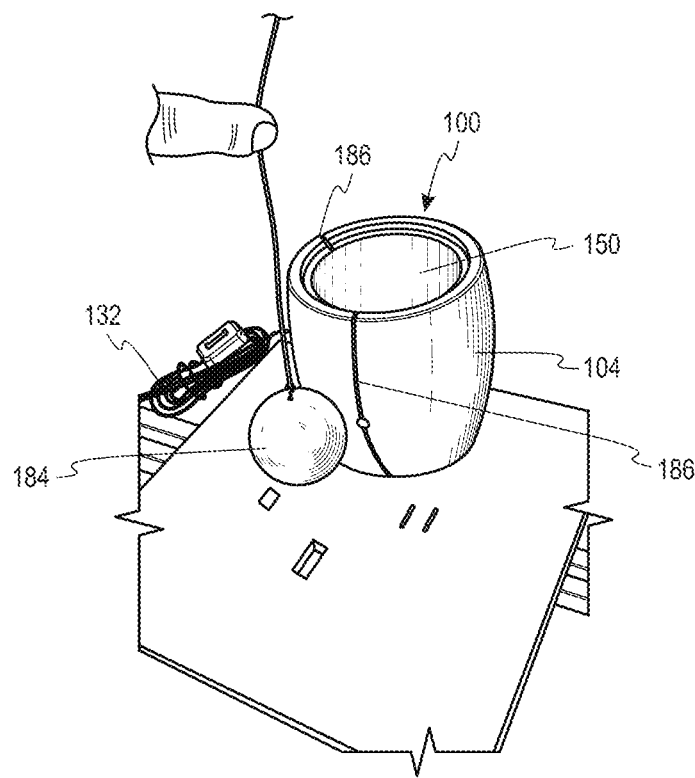
FIG. 8 is an image of a wax warmer undergoing a ball impact test.

Turning now to FIGS. 8 and 9, the embodiments of the wax warmer 100 are shown after a ball impact test is performed as required by the UL 283 standard for air fresheners and deodorizers. First, a steel ball 184 is configured to impact the body 104 of the wax warmer 100 from a specified distance of approximately 60 centimeters. The steel ball 184 may weigh approximately 535 grams and have a diameter of about 5.08 centimeters. As shown in FIG. 8, after the steel ball 184 engages the body 104, cracks 186 may form and the electrical assembly (not shown) is unexposed and inaccessible to a user's finger. As shown in FIG. 9, the body 104 has been removed from the wax warmer 100 after impact of the steel ball 184 and shows the electrical barrier 156 shielding the electrical assembly. Thus, the wax warmer 100 has passed the ball impact test according to the UL 283 standard. More specifically, although cracks 186 are present on the body 104, a finger probe (not shown) is incapable of contacting the electrical assembly 152 of the wax warmer 100 due to the presence of the electrical barrier 156. According to the UL 283 standard, if the finger probe can contact the electrical components through the broken ceramic housing, the wax warmer does not pass the ball impact test.

In contrast, conventional wax warmers typically fail the ball impact test since an electrical barrier is not present. Once the steel ball impacts a conventional wax warmer, the ceramic body breaks and the electrical components are exposed. A user and/or a finger probe can contact the live electrical components, making conventional wax warmers non-compliant with the UL 283 standard.

The wax warmer 100 in the embodiments depicted herein may be assembled quickly and efficiently. A wire harness (not shown) is first connected to the heater assembly 108, the electrical light source 130, and the electrical cord 132. It is contemplated that the electrical cord 132 may be replaced by batteries (not shown) contained within the body 104. It is further contemplated that any suitable electrical power source know to those having ordinary skill in the art may suffice. The next step in assembly is to insert the electrical assembly 152 (i.e., the heater assembly 108 and the electrical light source 130) into the interior space 116 of the body 104. Next, the electrical barrier 156/256 is inserted into the interior space 116 of the body 104 to surround the electrical assembly 152. Lastly the base plate 126 is attached to the bottom end 112 of the body 104.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmer that utilizes wax melts or the like.

INDUSTRIAL APPLICABILITY

A wax warmer is presented that provides an electrical barrier. Thus, a user may be inhibited from contacting live electrical components in the event that the wax warmer is damaged.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A wax warmer, comprising:
   a body;
   a top plate disposed adjacent a top end of the body;
   a base plate disposed adjacent a bottom end of the body;
   a reservoir supported by the top end of the body, the reservoir configured to receive a wax melt;
   an electrical assembly positioned within an interior space of the body; and
   a sleeve forming an electrical barrier positioned within the interior space and surrounding the electrical assembly, wherein a top edge of the sleeve is in contact with the top plate and a bottom edge of the sleeve is in contact with the base plate, and wherein the sleeve provides a barrier to the electrical assembly.

2. The wax warmer of claim 1, wherein the interior space is defined between the top plate, the base plate, and the body.

3. The wax warmer of claim 2, wherein the sleeve is integrally coupled to at least one of the base plate and the top plate.

4. The wax warmer of claim 1, wherein the sleeve is annular in shape.

5. A wax warmer, comprising:
   a body;
   an electrical assembly positioned within an interior space of the body; and
   an annular sleeve including a first side edge and a second side edge, wherein a groove is provided adjacent the first side edge configured to receive a tongue provided adjacent the second side edge, and wherein the annular sleeve is positioned within the interior space and surrounding the entire electrical assembly within the body.

6. The wax warmer of claim 5, wherein the electrical assembly includes a heat source that produces a heat output between about 10 watts and about 20 watts, and wherein the annular sleeve has a melting point of between about 350 to about 510 degrees Fahrenheit.

7. The wax warmer of claim 5, wherein the annular sleeve is distanced from the electrical assembly, the distance being measured from an interior surface of the annular sleeve to an exterior surface of the electrical assembly, the distance having a minimum length of about 0.3 centimeters.

8. The wax warmer of claim 7, wherein the electrical assembly includes a heat source and a ratio of the heat output of the heat source and a predetermined melting temperature of the annular sleeve is between about 0.02 and 0.05.

9. The wax warmer of claim 7, wherein the annular sleeve is distanced from the body of the wax warmer, the distance being measured from an exterior portion of the annular sleeve to an interior portion of the body.

* * * * *